(12) United States Patent
Piantoni et al.

(10) Patent No.: US 10,610,418 B2
(45) Date of Patent: Apr. 7, 2020

(54) DEVICE AND METHOD FOR LASER CUTTING A WEB OF FIBROUS MATERIAL

(71) Applicants: GDM S.p.A., Bologna (IT); UNIVERSITA' DEGLI STUDI DI BERGAMO, Bergamo (IT)

(72) Inventors: Matteo Piantoni, Albino (IT); Valerio Soli, Bologna (IT); Davide Russo, Florence (IT); Paolo Carrara, Sovere (IT)

(73) Assignees: GDM S.P.A., Bologna (IT); UNIVERSITA'DEGLISTUDI DI BERGAMO, Bergamo (IT)

( * ) Notice: Subject to any disclaimer, the term of this patent is extended or adjusted under 35 U.S.C. 154(b) by 603 days.

(21) Appl. No.: 15/305,054

(22) PCT Filed: Apr. 14, 2015

(86) PCT No.: PCT/IB2015/052691
§ 371 (c)(1),
(2) Date: Oct. 18, 2016

(87) PCT Pub. No.: WO2015/159204
PCT Pub. Date: Oct. 22, 2015

(65) Prior Publication Data
US 2017/0189242 A1 Jul. 6, 2017

(30) Foreign Application Priority Data

Apr. 18, 2014 (IT) .................. B02014A0226

(51) Int. Cl.
*B23K 26/38* (2014.01)
*A61F 13/15* (2006.01)
(Continued)

(52) U.S. Cl.
CPC .. *A61F 13/15723* (2013.01); *A61F 13/15764* (2013.01); *B23K 26/03* (2013.01);
(Continued)

(58) Field of Classification Search
CPC .......... A61F 13/15723; A61F 13/15764; A61F 2013/15821; B23K 26/082; B23K 26/032;
(Continued)

(56) References Cited

U.S. PATENT DOCUMENTS 5,444,212 A * 8/1995 MacNaughton ... B23K 26/0846
219/121.7
5,690,846 A * 11/1997 Okada ................ B23K 26/0853
219/121.71
(Continued)

FOREIGN PATENT DOCUMENTS

CN 1537520 A 10/2004
CN 101203353 A 6/2008
(Continued)

OTHER PUBLICATIONS

Japanese Office Action dated Dec. 26, 2018 for counterpart Japanese Patent Application No. 2016-563047.
(Continued)

*Primary Examiner* — Chee-Chong Lee
(74) *Attorney, Agent, or Firm* — Shuttleworth & Ingersoll, PLC; Timothy J. Klima

(57) ABSTRACT

A device for cutting a web of fibrous material including movement means for moving a web of fibrous material to be cut, defining a feed surface for the web and having at least one first cutting zone, at least one laser source configured to generate a laser beam extending along its operating direction towards the first cutting zone to make, on the web, at least one incision extending along a predetermined cutting line, where a portion of the laser beam passes through the web of
(Continued)

fibrous material at the first cutting zone. The device also includes recovery means for recovering the portion of the laser beam and at least partly located along the operating direction, at the first cutting zone, in such a way as to intercept the portion of the laser beam and direct it towards a second cutting zone to make a further incision or cut.

16 Claims, 4 Drawing Sheets

(51) Int. Cl.
*B23K 26/08* (2014.01)
*B23K 26/03* (2006.01)
*B23K 26/36* (2014.01)
*B23K 101/22* (2006.01)

(52) U.S. Cl.
CPC ...... *B23K 26/0823* (2013.01); *B23K 26/0846* (2013.01); *B23K 26/36* (2013.01); *B23K 26/38* (2013.01); *B23K 2101/22* (2018.08)

(58) Field of Classification Search
CPC ................ B23K 26/08; B23K 26/0846; B23K 2103/40; B23K 26/03; B23K 26/0823; B23K 26/36; B23K 26/38; B23K 2101/22
USPC .................................................. 239/121.67
See application file for complete search history.

(56) References Cited

U.S. PATENT DOCUMENTS 6,974,930 B2 * 12/2005 Jense ................. B23K 26/0846
  219/121.8
7,528,343 B2    5/2009 Lupinetti et al.
9,149,394 B2   10/2015 Rosani et al.

FOREIGN PATENT DOCUMENTS

| | | |
|---|---|---|
| CN | 103402472 A | 11/2013 |
| EP | 1047364 B1 | 7/2004 |
| EP | 1447068 A1 | 8/2004 |
| JP | S4935998 A | 4/1974 |
| JP | S52125194 U | 9/1977 |
| JP | 3111483 U | 7/2005 |
| JP | 201327933 A | 7/2013 |
| WO | WO03022510 A1 | 3/2003 |
| WO | 2008015550 A2 | 2/2008 |
| WO | WO2008015550 | 2/2008 |

OTHER PUBLICATIONS

International Search Report and Written Opinion dated Sep. 22, 2015 for related PCT Application No. PCT/IB2015/052691.
Chinese Office Action dated Apr. 3, 2019 from counterpart Chinese App No. 201580020283.
Chinese Search Report dated Mar. 26, 2019 from counterpart Chinese App No. 201580020283.

* cited by examiner

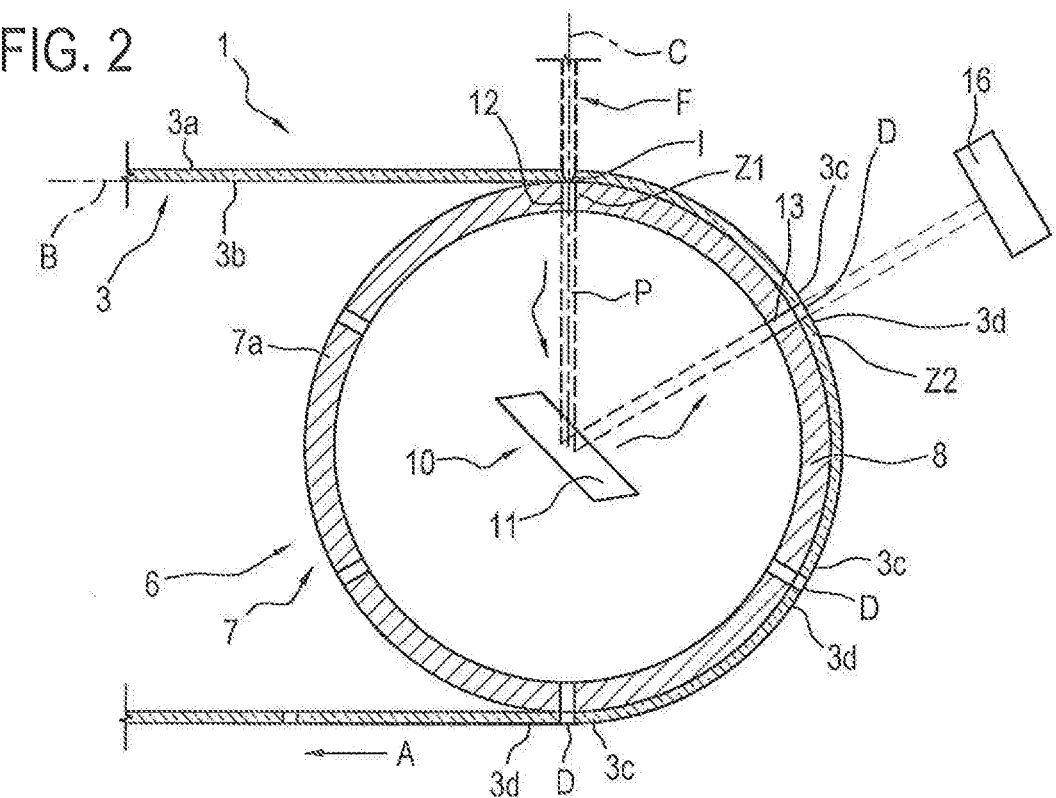
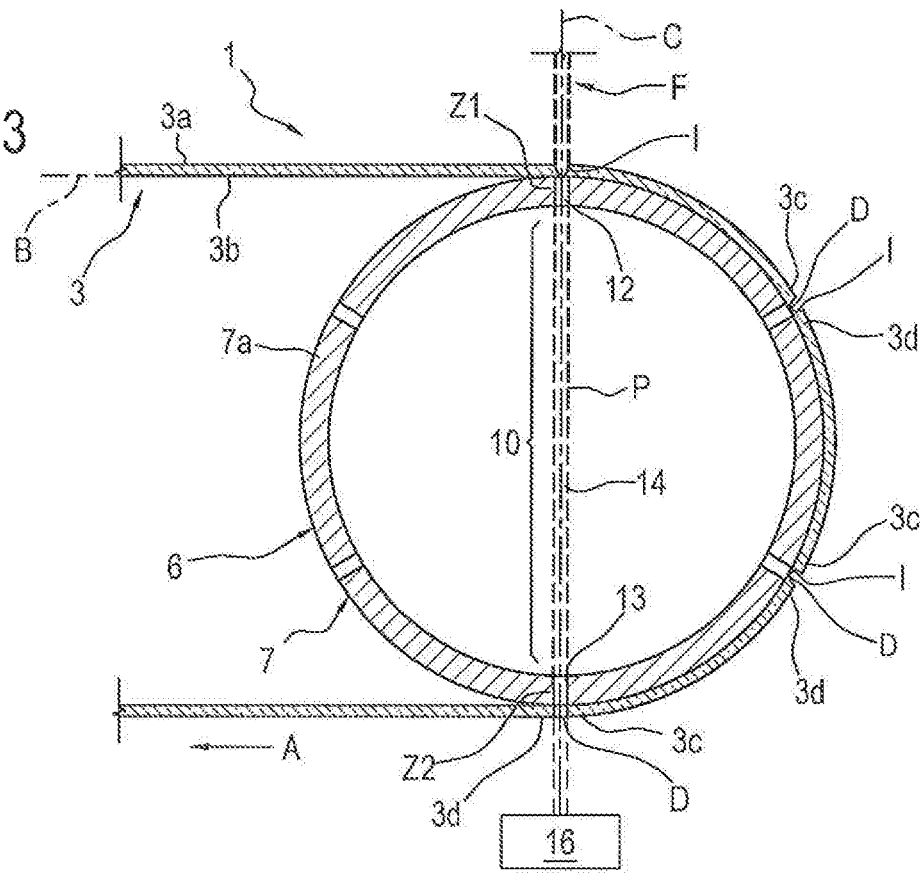

DEVICE AND METHOD FOR LASER CUTTING A WEB OF FIBROUS MATERIAL

This application is the National Phase of International Application PCT/IB2015/052691 filed Apr. 14, 2015 which designated the U.S.

This application claims priority to Italian Patent Application No. BO2014A000226 filed Apr. 18, 2014, which application is incorporated by reference herein.

TECHNICAL FIELD

This invention relates to a device and a method for laser cutting a web of fibrous material, preferably a continuous web.

More specifically, this invention applies to the manufacture of sanitary underwear such as baby nappies, sanitary towels or the like.

BACKGROUND ART

These sanitary articles typically comprise an absorbent pad which is normally sandwiched between a permeable inner layer of non-woven fabric and an impermeable outer layer of polyethylene.

The manufacture of such articles involves the formation initially of a continuous web incorporating the aforementioned layers, then shaping the web and finally separating the web into single items ready for packaging.

Shaping consists mainly in the cutting of leg contours and, more generally, serves to give the article an outline appropriate for the specified use.

These operations thus necessitate cutting the material and prior art devices used for this type of operation comprise a rotating drum, around which the web is looped partially as it advances in a predetermined direction, and a laser cutting head that operates on the web in the course of its passage over the drum. Laser cutting heads are especially suitable for processes used in the manufacture of sanitary underwear products, by virtue of their low maintenance requirements and their ease of control and adjustment, especially when compared with rotary blade cutter systems adopted in this same technical field, which require frequent replacement of the blades, or at all events, frequent sharpening of the blades.

While the pros of such an application are evident, one disadvantage of using laser cutting is, without doubt, that connected with the cost and overall dimensions of laser generators.

Indeed, although the laser source is designed to bring the entire thickness of the web to sublimation, the presence of mainly fibrous material means that, in many parts of the web, the laser beam passes through the web without coming into contact with the material.

In other words, although the power (and hence the cost and dimensions) of the laser source is such that it is able to cut the web, a large part of the beam is not used.

DISCLOSURE OF THE INVENTION

In light of the above, the primary technical purpose of this invention is to devise a device and a method for laser cutting a web of fibrous material and capable of overcoming the above mentioned disadvantages.

In the context of this technical purpose, one important aim of the invention is to provide a device and a method of low cost and reduced overall dimensions for laser cutting a web of fibrous material.

A further aim of the invention is to devise a method and a device for laser cutting a web of fibrous material allowing less waste of energy from the laser source.

The technical purpose and aims specified are substantially achieved by a device for laser cutting a web of fibrous material comprising the technical features set out in claim 1.

The aims specified are also achieved by a method for laser cutting a web of fibrous material comprising the technical features set out in claim 9.

BRIEF DESCRIPTION OF DRAWINGS

Further features and advantages of this invention are more apparent in the non-limiting description of a preferred but non-exclusive embodiment of a device for laser cutting a web of fibrous material, as illustrated in the accompanying drawings, in which:

FIG. 2 illustrates a first variant embodiment of the device for laser cutting a web of fibrous material of FIG. 1;

FIG. 3 illustrates a second variant embodiment of the device for laser cutting a web of fibrous material of FIG. 1;

DETAILED DESCRIPTION OF PREFERRED EMBODIMENTS OF THE INVENTION

Figure 1:
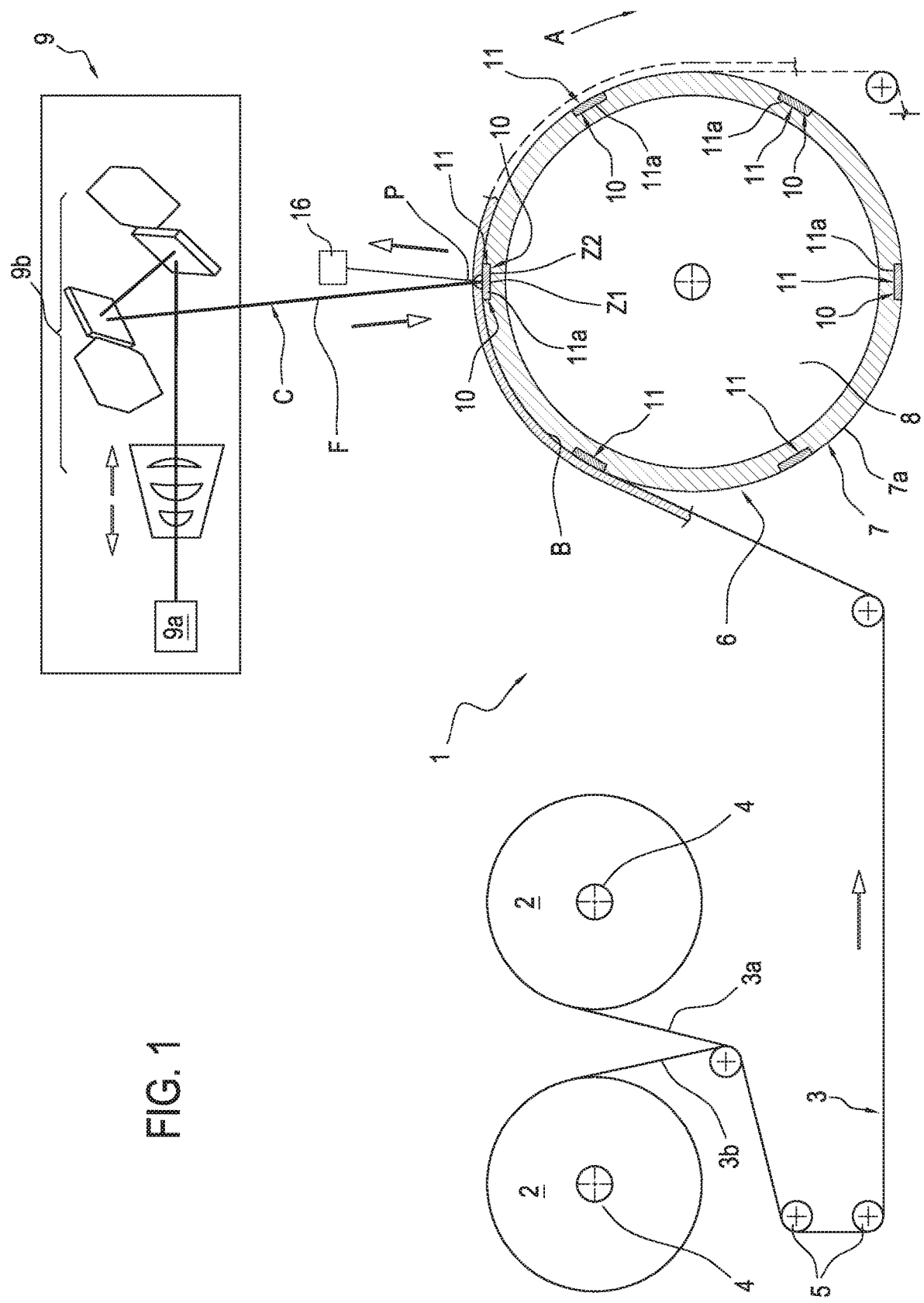
FIG. 1 shows a schematic side view of a first embodiment of a device according to this invention for laser cutting a web of fibrous material.
Figure 1A:
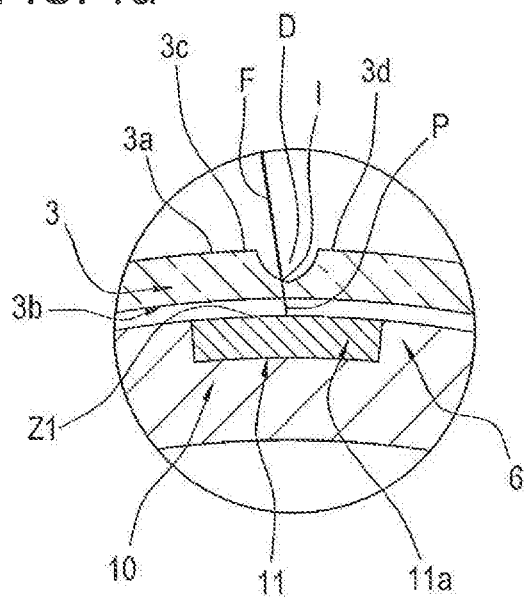
FIGS. 1a, 1b, 1c are details of the cutting zone of the device of FIG. 1.
Figure 1B:
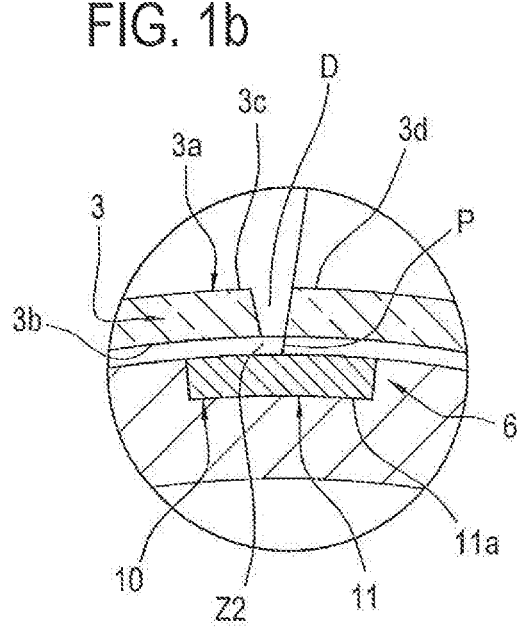
Figure 1C:
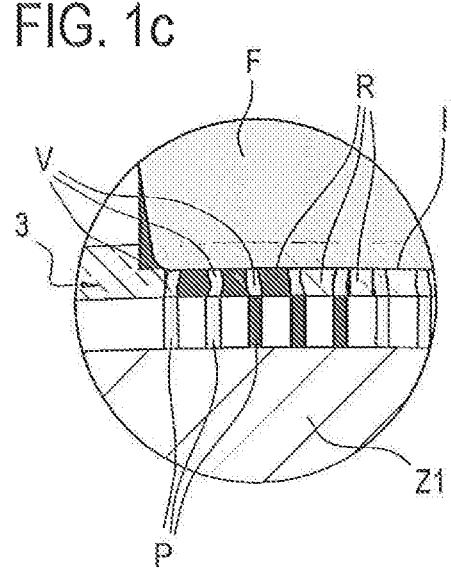

With reference to the accompanying drawings, the numeral 1 denotes a device for laser cutting a web 3 of fibrous material.

Preferably, therefore, the material the web 3 is made of is fibrous, that is to say, it has empty zones "V" alternated with full zones "R".

In other words, the web 3 is made of at least one variable density material whose fibres, being discrete, define free portions, that is, empty zones.

It should be noted that in some applications, the device 1 according to the invention can also be used to cut other kinds of materials, having an even structure.

Preferably, the device 1 is fitted in a machine for making sanitary underwear such as baby nappies or sanitary towels.

The device thus comprises an unwinder 2, illustrated schematically since it is of known type, at which a web 3, preferably continuous and padded, is made, for example by juxtaposing a first layer 3a of permeable material with a second layer 3b of impermeable material and interposing between the two a portion of absorbent material, not illustrated, constituting the padding. This operation is done, for example, by two feed rollers 4 and a device of known type, not illustrated in the drawings, for adding the pad.

Next, the continuous web 3 thus made is made to advance by means of suitable movement means 6 configured to impart motion to the web 3 of material to be cut and defining a feed surface "B".

More precisely, the movement means 6 comprise at least a conveyor 7 around which the web 3 is at least partly wound and constituting for the same a feed direction "A."

Preferably, the conveyor 7 comprises an outer mantle 7a movable along the feed direction "A" and constituting a supporting element for the web 3 Thus, the mantle 7a constitutes the feed surface "B".

In this configuration, the continuous web 3, as it advances along the direction "A", is thus accompanied by a rotational movement of the mantle 7a, to avoid rubbing between the continuous web 3 and the mantle 7a itself.

In the preferred embodiment, the conveyor 7 is defined preferably by a rotating drum 8 so that the continuous web 3 is at least partly wound around the rotating drum 8.

Preferably, to guarantee processing precision, the device is equipped with tensioning means 5 (of essentially known type) operatively located upstream of the conveyor 7.

More preferably, further tensioning means 4 are operatively located downstream of the conveyor 7 (that is, of the rotating drum 8) to pass the web 3 on for further processing.

According to the object of this invention, the movement means 6 (that is, the conveyor 7) are provided at least with a first cutting zone Z1, where at least a first cut (or incision/pre-cut) is made on the web 3.

More precisely, a second cutting zone Z2 is also defined along the movement means 6.

Thus, the first cutting zone Z1 and the second Z2 are located along the feed direction "A".

It should be noted that in some embodiments of this invention, the first cutting zone Z1 and the second Z2 coincide, as will become clearer from the examples described below.

In order to cut the material, the device 1 also comprises a laser source 9a configured to generate a laser beam "F" extending along its operating direction "C" towards the first cutting zone Z1 to make, on the web 3, at least one incision "I" extending along a preset cutting line "D".

It should be noted that the cutting line "D" is interposed between a first edge 3c and a second edge 3d of the web.

Preferably, the laser source 9a is associated with a cutting head 9 facing the movement means 6, in particular the first cutting zone Z1, and configured to move the laser beam "F" along the aforesaid cutting line "D".

Thus, the cutting head 9 comprises both the laser source 9a and an optical system 9b configured to direct the laser beam "F" at the cutting zone Z1.

It should be noted that the cutting line "D", and hence the incision "I", preferably defines a straight or curved line (defining, for example, the leg contours of the sanitary article).

Alternatively, however, the laser source 9a (and hence the cutting head 9) might be used to make the full peripheral profiles of the articles to be made. In other words, the cutting line "D" might also be a closed line.

Considering the structure of the material the web 3 is made of, that is, a fibrous material with empty zones "V" alternated with full zones "R", at least one portion "P" of the laser beam "F" passes through the web 3.

Thus, the laser beam "F" has at least one portion "P" which passes through the web 3 by way of the empty zones "V", that is, without encountering any obstacles.

The beam "F" is, instead, partly absorbed by the full zones "R" of the material to make an incision or cut.

According to one aspect of the invention, the laser source 9a (or the cutting head 9) is configured to use the laser beam "F" at the first cutting zone Z1 to make along the cutting line "D" an incision "I" in the material without separating the first edge 3c from the second edge 3d.

Preferably, the power of the laser source 9a is rated as a function of the material to be cut so that the portion "P" which passes through the material in the cutting zone Z1 has a predetermined energy content.

The cutting head 9 comprises at least a mirror scanning apparatus for cutting the continuous web 3 along the aforementioned cutting paths.

Advantageously, the laser cutting head 9 is associated with an adjustment device (not illustrated) for adjusting the initial position of the cutting head 9. The adjustment device acts on the transversal and/or longitudinal movement of the cutting head 9 in such a way that the movement of the head 9 relative to the web 3 allows making the desired profiles (that is, defines the cutting line "D"). This device also adjusts the movement of the head 9 as a function of the feed speed of the continuous web 3, so as to trace the set profiles on the continuous web 3 even when the feed speed of the web 3 itself is varied.

In detail, the adjustment and rating device is provided with dedicated software which, once a specific cutting path has been saved, generates drive signals for moving the cutting head 9 (or the optical system 9b) in a suitable manner. Preferably, the cutting head 9 comprises suitable position transducers capable of detecting position and to communicate with the adjustment device to determine the consequent movement to be imparted to the cutting head 9.

According to the invention, the device 1 comprises recovery means 10 for recovering the portion "P" of the laser beam "F" and at least partly located along the operating direction "C", at the first cutting zone Z1, in such a way as to intercept the portion "P".

The recovery means 10 are configured to direct the portion "P" towards the second cutting zone Z2 in such a way as to make another cut or incision in the web 3 also in that zone using the energy content of a single laser source 9a.

Advantageously, that way, the power of the laser source and, more specifically, of the portion "P", which would otherwise be lost, can be used for further operations.

Preferably, the laser source 9a is configured to use the laser beam "F" at the first cutting zone Z1 to make along the cutting line "D" an incision "I" in the material without separating the first edge 3c from the second edge 3d.

In other words, the laser source 9a is power rated to generate a laser beam "F" which is unable to make a complete cut (that is, to separate the first portion 3c from the second 3d) in a single pass.

In light of this, the laser source 9a is configured to generate a laser beam "F" of preset power capable only of incising the web 3 of material, that is, of making a partial cut.

In the preferred embodiment, the laser source 9a is also power rated in such a way that the recovered portion "P" of the laser beam "F" makes at the second cutting zone Z2 and along the cutting line "D", a full cut by which the first edge 3c is completely separated from the second edge 3d.

In other words, the cutting device 1 is configured to make a pre-cut (or incision "I") at the first cutting zone Z1 and to complete the cut at the second cutting zone Z2 by recovering and directing the aforementioned portion "P" of the laser beam through the recovery means 10.

Advantageously, this allows considerably reducing the power (and thus the cost and size) of the laser source 9a (or of the head 9) while still allowing a complete and precise cut to be made in the web 3 using that portion of the laser which would otherwise be lost.

In other words, the cut is no longer made in a single operation but in two steps, one for incising (or pre-cutting) and the other for cutting, using the power of the single laser beam "F".

This has the advantage of concurrently minimizing the size of the laser source 9 and the quantity of energy dissipated (or unused) after cutting.

In light of this, it is no longer necessary for the power of the laser beam "F" to be such as to cut the material in a single pass but it is sufficient for it to make a percentage of the cut (preferably variable between 50 and 70%), which is then completed by recovering the remaining portion "P" of the beam "F".

Preferably, the recovery means 10 are operatively located downstream of the first cutting zone Z1, in the proximity thereof, in order to intercept the portion "P" of the laser beam and direct it towards the second cutting zone Z2. Thus, the recovery means 10 are at least partly located along an optical path of the laser beam "F".

More precisely, the feed surface "B" is operatively interposed between the laser source 9a (that is, the cutting head 9) and the recovery means 10.

Preferably, the recovery means 10 comprise at least one reflecting member 11 located along the operating direction "C" and oriented in such a way as to reflect the portion "P" of the laser beam towards the second cutting zone Z2.

In other words, in these embodiments, the recovery of the portion "P" of the laser beam occurs by the reflection thereof in the direction of the web 3, and more specifically, in the direction of the second cutting zone Z2.

The reflecting member is preferably a metallic part made of one of the following materials:
molybdenum;
aluminium;
copper
silicon (in this case preferably having a protective coating).

With reference to FIG. 1, the first cutting zone Z1 and the second cutting zone Z2 substantially coincide with each other.

In other words, reflection of the portion "P" of the laser beam is not delocalized but occurs directly at the first cutting zone Z1.

In this regard, the reflecting member 11 is associated with the movement means 6 in such a way as to at least partly define the feed surface "B" and is oriented in such a way as to reflect the portion "P" of the laser beam on the cutting line "D" at the first cutting zone Z1 (which, as stated, coincides with the second cutting zone Z2).

Thus, the reflecting member is associated with the mantle 7a of the conveyor 7.

In this embodiment, the reflecting member 11 may be the mantle itself or it may be a metallic insert 11a located at the first cutting zone Z1.

Preferably, also, there is a filtering unit 16 operatively located downstream of the second cutting zone Z2 to intercept and absorb the laser residue, if any, which might pass through the web 3 again.

Advantageously, this avoids problems connected with back reflection.

Figure 4:
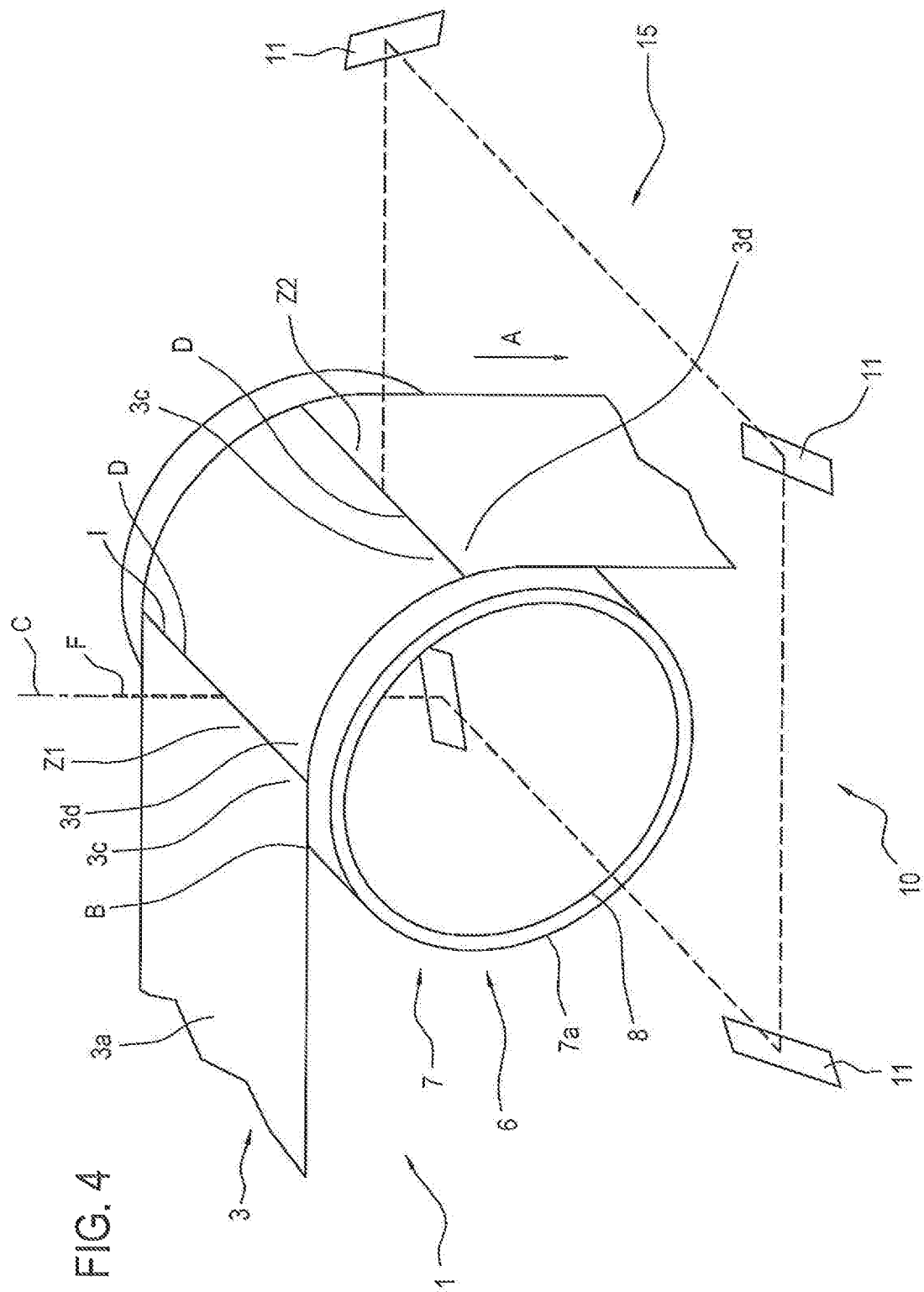
FIG. 4 illustrates a third variant embodiment of the device for laser cutting a web of fibrous material of FIG. 1.

Alternatively, with reference to FIGS. 2 and 4, the movement means 6 are provided, at the first cutting zone Z1, with a permeable portion 12 permeable to the laser beam "F" to allow through it the portion "P" which passes through the web 3.

The expression "permeable portion 12" is used in this text to mean a zone of the movement means 6 which allows the laser beam "F", and more specifically, the portion "P" thereof, to pass through.

More precisely, it is the supporting element of the movement means 6 (that is, the mantle 7a of the conveyor 7) which is provided with the permeable portion 12, that is to say, a zone which the portion "P" of the laser beam can pass through.

The recovery means 10 are thus operatively located downstream of the permeable portion 12, with reference to the aforementioned optical path of the laser beam "F", in such a way as to intercept the portion "P" of the laser beam which passes through the permeable portion 12 and direct it towards the second cutting zone Z2.

Thus, in this embodiment, the first cutting zone Z1 and the second cutting zone Z2 are distinct and spaced from each other along the feed direction "A".

It should be noted that the permeable portion 12 may be embodied by a through opening or slot, or by an insert or window transparent to the laser beam "F".

Provided below by way of example (non exhaustive) are some lists of materials which can be used for this purpose, according to the type of laser:

| $CO_2$ LASER: | |
| --- | --- |
| Barium fluoride | $BaF_2$ |
| Zinc selenide | ZnSe |
| Gallium arsenide | GaAs |
| Germanium | Ge |
| Cadmium telluride | CdTe |
| Cadmium magnesium telluride | CdMgTe |
| Cadmium manganese mercury telluride | CdMnHgTe |
| Cadmium manganese telluride | CdMnTe |
| Amorphous quartz | $SiO_2$ |
| Potassium bromide | KBr |
| Potassium chloride | KCl |
| Silver bromide | AgBr |
| Silver chloride | AgCl |
| Sodium chloride | NaCl |
| Thallium bromo-iodide | TlBr—TlI |

| DIODE: | |
| --- | --- |
| Barium fluoride | $BaF_2$ |
| Zinc selenide | ZnSe |
| Gallium arsenide | GaAs |
| Germanium | Ge |
| Cadmium magnesium telluride | CdMgTe |
| Cadmium manganese mercury telluride | CdMnHgTe |
| Cadmium manganese telluride | CdMnTe |
| Amorphous quartz | $SiO_2$ |
| Potassium bromide | KBr |
| Potassium chloride | KCl |
| Silver bromide | AgBr |
| Silver chloride | AgCl |
| Sodium chloride | NaCliBr |
| Thallium bromo-iodide | TlBr |
| Borosilicate glass | BK-7 |
| Calcium fluoride | $CaF_2$ |
| Magnesium fluoride | $MgF_2$ |
| Sapphire | $Al_2O_3$ |

| QCL: | |
| --- | --- |
| Barium fluoride | $BaF_2$ |
| Zinc selenide | ZnSe |
| Gallium arsenide | GaAs |
| Germanium | Ge |
| Cadmium magnesium telluride | CdMgTe |
| Cadmium manganese mercury telluride | CdMnHgTe |
| Cadmium manganese telluride | CdMnTe |
| Amorphous quartz | $SiO_2$ |
| Potassium bromide | KBr |
| Potassium chloride | KCl |

-continued

| QCL: | |
|---|---|
| Silver bromide | AgBr |
| Silver chloride | AgCl |
| Sodium chloride | NaCliBr |
| Thallium bromo-iodide | TlBr |
| Cadmium telluride | CdTe |
| Calcium fluoride | CaF2 |
| Magnesium fluoride | MgF2 |
| Sapphire | Al2O3 |
| Silicon | Si |

In the second case, means are provided for cleaning the insert or window, configured to remove the dirt produced by the sublimation of the fibrous material.

Preferably, therefore, the reflecting member 11 of the recovery means 10 is operatively located downstream of the permeable portion 12. In the embodiment illustrated, the reflecting member 11 is located inside the drum 8 to intercept the portion "P" and reflect it to the second cutting zone Z2.

Preferably, the movement means 6 (that is, the mantle 7a of the conveyor, and thus the drum 8) are provided with a further permeable portion 13 operatively located downstream of the reflecting member 11 and aligned with a direction of propagation of the portion "P" of the laser beam reflected by the selfsame reflecting member 11. The further permeable portion 13 thus defines the second cutting zone Z2.

It should be noted that the further permeable portion 13, too, may be embodied by a slot, or by a laser transparent insert or window.

In this embodiment, therefore, the laser beam "F" acts on the first cutting zone Z1 on a first face (preferably external and corresponding to the first layer 3a) of the web 3, whilst the portion "P" acts on the second cutting zone Z2 on a second face (preferably internal and corresponding to the second layer 3b) of the web 3.

It should be noted that the orientation of the reflecting member 11, that is, the phase displacement between the beam portion "P" upstream and downstream of the reflecting member 11, is preferably a function of the cutting speed and of the angular speed of the drum.

Alternatively, with reference to FIG. 4, the recovery means 10 might comprise a plurality of reflecting members 11, constituting a system of mirrors 15 positioned to guide the portion "P" onto the first face 3a of the web 3.

In this embodiment, therefore, the optical path of the laser beam portion "P" is defined by a plurality of stretches at an angle to each other at respective reflecting members 11.

In order to keep the reflecting surface of the reflecting member 11 clean (in particular with reference to the solution of FIG. 1), cleaning means (not illustrated) are preferably provided.

These cleaning means may be pneumatic, ultrasound or contact cleaning means.

To avoid the cleaning problem, with reference to FIG. 3, the recovery means 10 might be defined by a straight duct 14 aligned with the operating direction "A" of the laser beam "F".

In the embodiment illustrated, they are aligned along a straight direction corresponding to the operating direction "A".

More precisely, the permeable portion 12 and the further permeable portion 13 are made in opposite half-parts of the drum 8.

Similarly, therefore, the first cutting zone Z1 and the second cutting zone Z2 (defined by the slots 12, 13) are aligned along that direction.

Advantageously, in cutting devices 1 which make only one cut (that is, one incision and one cut) per turn, this does away with the need for reflecting members.

It should be noted that, depending on the embodiment, the cut may be made in two passes of a single laser beam (FIG. 1) or in two passes of two distinct laser beams (FIGS. 2-4).

In effect, in the embodiment of FIG. 1, for example, the portion "P" is reflected directly in the first cutting zone Z1, that is to say, instantaneously.

In the embodiments of FIGS. 2-4, on the other hand, the two cutting steps (incision and cut) are performed in two distinct zones of the movement means 6, meaning that a single laser beam "F" is used to make the incision "I" in one zone of the web 3, whilst its respective portion "P" is used to complete the cut in another, previously incised zone.

This invention also has for an object a method for cutting a web 3 of material, the method being preferably implemented by means of the cutting device 1 described above.

The method thus comprises a step of preparing a laser source 9a and a step of preparing a web 3 of material to be cut.

More precisely, the web 3 is positioned in a predetermined first cutting zone Z1.

The method also comprises generating a laser beam "F" and directing that portion towards the first cutting zone Z1 in order to perform one operation on the web.

More precisely, the laser beam "F" is used to make on the web 3 an incision "I" extending along a predetermined cutting line "D" (described above in connection with the device 1).

It should be noted that while the incision "I" is being made, a portion "P" of the laser beam "F" passes through the web 3.

More precisely, the portion "P" passes at least through the empty zones "V" of the material the web 3 is made of.

Thus a beam portion "P" whose intensity (or energy content) is less than that of the laser beam "F", passes through the web 3 from one face to the other.

According to the invention, the method comprises a step of recovering the laser beam portion "P" which has passed through the web 3 and a step of directing it towards a second cutting zone Z2 (where the web has been positioned).

More precisely, the power of the laser beam "F" is such that the step of making the incision "I" does not completely separate the first edge 3c and the second edge 3d of the web 3 from each other.

Further, the step of directing the recovered laser beam portion "P" is accomplished by directing the portion "P" along the cutting line "D" in such a way as to separate the first edge 3c from the second edge 3d thereby completing the cutting of the web 3 along the cutting line "D".

Thus, the power of the beam portion "P" which passes through the web at the first cutting zone Z1 is such that the directing step has the effect of separating the first edge 3c and the second 3d from each other (that is, the cut is completed).

Advantageously, therefore, it is possible to complete the cutting of the web 3 along the cutting line "D" by performing two steps in sequence (incising and cutting) using the energy contained in a single laser beam "F".

Preferably, the step of recovering the portion "P" of the laser beam "F" comprises at least one sub-step of reflecting and/or concentrating the selfsame portion "P" on the second cutting zone Z2.

Similarly to what was described above in connection with the cutting device, the reflecting sub-step may be direct or delocalized.

In the first embodiment, where the reflecting sub-step is direct, the first cutting zone Z1 and the second cutting zone Z2 are substantially coincident.

In other words, the steps of recovering and directing the portion "P" of the laser beam "F" are defined by a step of directly reflecting the portion "P" itself in the same cutting zone from which it comes (that is, the first cutting zone Z1, which coincides with the second cutting zone Z2). Thus, in this embodiment, the incising step and the cutting step are substantially simultaneous.

In the second embodiment, on the other hand, the first cutting zone Z1 and the second Z2 are distinct and spaced from each other along a feed path or direction "A" of the web 3.

That way, advantageously, the energy of the laser beam "F" can be recovered and re-directed in the most suitable way, according to applications.

The invention described brings important advantages.

In effect, recovering the laser beam portion that would otherwise be lost allows precision cutting of the web while at the same time limiting the power of the laser source required.

Besides, using a device of this kind in the manufacture of absorbent sanitary articles, made mainly of fibrous material, is particularly advantageous and allows recovery of up to 50% of the energy.

Moreover, using the beam portion which passes through the web allows limiting, or minimizing, the laser beam energy which remains unused, which means that energy efficiency is increased.

The invention claimed is:

1. A device for cutting a web of fibrous material, comprising:
    the web of fibrous material;
    a rotatable drum for moving the web, where the web includes a variable density material having a discrete distribution of fibers defining solid zones and empty zones free from material, the rotatable drum also defining a feed surface for the web and including a first cutting zone;
    a laser source configured to generate a laser beam extending along an operating direction towards the first cutting zone to make, on the web, an incision extending along a predetermined cutting line interposed between a first edge and a second edge of the web, wherein, at the first cutting zone, the laser beam is partly absorbed by the solid zones to make the incision and a portion of the laser beam passes through the web via the empty zones;
    a recovery system including at least one chosen from a mirror and a permeable portion of the rotatable drum for recovering the portion of the laser beam and at least partly located along the operating direction, at the first cutting zone, in such a way as to intercept the portion of the laser beam and direct the portion of the laser beam towards a second cutting zone to make a further incision on the web;
    wherein the laser source and the recovery system are configured to:
        use the laser beam at the first cutting zone to make the incision along the predetermined cutting line without separating the first edge from the second edge;
        use the portion of the laser beam at the second cutting zone to make the further incision along the predetermined cutting line by which the first edge is completely separated from the second edge.

2. The device according to claim 1, wherein the feed surface is operatively interposed between the laser source and the recovery system.

3. The device according to claim 2, wherein the mirror is associated with the rotatable drum to at least partly define the feed surface and is oriented to reflect the portion of the laser beam on the cutting line at the first cutting zone.

4. The device according to claim 1, wherein the recovery system comprises the mirror located along the operating direction and oriented in such a way as to reflect the portion of the laser beam towards the second cutting zone.

5. The device according to claim 4, wherein the first cutting zone and the second cutting zone are coincident.

6. The device according to claim 1, wherein the rotatable drum comprises, for the web, at least one supporting element provided, at the first cutting zone, with a permeable portion permeable to the laser beam "F" to allow through the permeable portion the laser beam portion which passes through the feed surface; the recovery system being operatively located downstream of the permeable portion, with reference to an optical path of the laser beam, to intercept the laser beam portion which passes through the permeable portion and direct the laser beam portion towards the second cutting zone.

7. The device according to claim 6, wherein the permeable portion is defined by a through slot.

8. The device according to claim 6, wherein the permeable portion is defined by an insert or window which is transparent to the laser beam; the device comprising a cleaning device, including at least one chosen from a pneumatic device, an ultrasound device and a contact device, for cleaning the insert or window, configured to remove dirt produced by sublimation of the fibrous material.

9. The device according to claim 6, wherein the mirror is operatively located downstream of the permeable portion, with reference to an optical path of the laser beam, and oriented in such a way as to reflect the portion of the laser beam onto the second cutting zone which is distinct from the first cutting zone.

10. The device according to claim 1, wherein the rotatable drum establishes a feed direction for the web, with the web being at least partly wound around the rotatable drum during operation of the device.

11. A method for cutting a web of material, comprising the steps of:
    providing a device for cutting a web of fibrous material, comprising:
        the web of fibrous material;
        a rotatable drum for moving the web, where the web includes a variable density material having a discrete distribution of fibers defining solid zones and empty zones free from material, the rotatable drum also defining a feed surface for the web and including a first cutting zone;
        a laser source configured to generate a laser beam extending along an operating direction towards the first cutting zone to make, on the web, an incision extending along a predetermined cutting line interposed between a first edge and a second edge of the web, wherein, at the first cutting zone, the laser beam is partly absorbed by the solid zones to make the incision and a portion of the laser beam passes through the web via the empty zones;
        a recovery system including at least one chosen from a mirror and a permeable portion of the rotatable drum for recovering the portion of the laser beam and at least partly located along the operating direction, at the first cutting zone, in such a way as to intercept the portion of the laser beam and direct the portion of the laser beam towards a second cutting zone to make a further incision on the web;

wherein the laser source and the recovery system are configured to:

use the laser beam at the first cutting zone to make the incision along the predetermined cutting line without separating the first edge from the second edge;

use the portion of the laser beam at the second cutting zone to make the further incision along the predetermined cutting line by which the first edge is completely separated from the second edge;

preparing the web;

positioning the web at the first cutting zone;

generating the laser beam directed towards the first cutting zone;

making in the web, using the laser beam, the incision extending along the cutting line in such a way that the portion of the laser beam, not used in making the incision, passes through the web at least through the empty zones;

recovering the portion of the laser beam which has passed through the web;

positioning the web at the second cutting zone;

directing the recovered laser beam portion towards the second cutting zone to make the further incision in the web.

12. The method according to claim 11, wherein the cutting line is interposed between the first edge and the second edge of the web; the power of the laser beam being such that the step of making the incision does not completely separate the first edge and the second edge from each other.

13. The method according to claim 11, wherein the cutting line is interposed between the first edge and the second edge of the web; the directing step being accomplished by directing the recovered laser beam portion along the cutting line in such a way as to separate the first edge from the second edge thereby completing the cutting of the web along the cutting line.

14. The method according to claim 11, wherein the step of recovering the portion of the laser beam comprises at least a sub-step of at least one chosen from reflecting and concentrating the portion of the laser beam on the second cutting zone.

15. The method according to claim 11, wherein the first cutting zone and the second cutting zone are substantially coincident.

16. The method according to claim 11, wherein the step of recovering and directing the portion of the laser beam are defined by a step of directly reflecting the portion of the laser beam onto the same cutting zone from which the portion of the laser beam comes.

* * * * *